US006826536B1

(12) United States Patent
Forman

(10) Patent No.: US 6,826,536 B1
(45) Date of Patent: Nov. 30, 2004

(54) HEALTH CARE BILLING MONITOR SYSTEM FOR DETECTING HEALTH CARE PROVIDER FRAUD

(76) Inventor: Bert Forman, 2708 Morton Ave., Oceanside, NY (US) 11572

( * ) Notice: Subject to any disclaimer, the term of this patent is extended or adjusted under 35 U.S.C. 154(b) by 804 days.

(21) Appl. No.: 09/620,320

(22) Filed: Jul. 22, 2000

(51) Int. Cl.[7] .......... G06F 17/60

(52) U.S. Cl. .......... 705/4; 705/3

(58) Field of Search .......... 705/2–3, 4, 38–40, 705/42, 44, 35; 379/114, 114.4

(56) References Cited

U.S. PATENT DOCUMENTS

| | | | | | |
|---|---|---|---|---|---|
| 5,253,164 | A | * | 10/1993 | Holloway et al. | 705/2 |
| 5,359,509 | A | * | 10/1994 | Little et al. | 705/2 |
| 5,544,044 | A | * | 8/1996 | Leatherman | 705/3 |
| 5,557,514 | A | * | 9/1996 | Seare et al. | 705/2 |
| 5,835,897 | A | * | 11/1998 | Dang | 705/2 |
| 5,970,463 | A | * | 10/1999 | Cave et al. | 705/3 |
| 5,991,758 | A | | 11/1999 | Ellard | 707/6 |
| 5,995,937 | A | | 11/1999 | DeBusk et al. | 705/2 |
| 6,058,380 | A | | 5/2000 | Anderson et al. | 705/40 |
| 6,070,141 | A | | 5/2000 | Houvener et al. | 705/1 |
| 6,223,164 | B1 | * | 4/2001 | Seare et al. | 705/2 |
| 6,253,186 | B1 | * | 6/2001 | Pendleton, Jr. | 705/2 |
| 6,324,516 | B1 | * | 11/2001 | Shults et al. | 705/2 |
| 6,370,511 | B1 | * | 4/2002 | Dang | 705/3 |

FOREIGN PATENT DOCUMENTS

WO PCT/US96/10352 * 3/1997

OTHER PUBLICATIONS

Lees Haley, Paul R., "Coping with exaggerated claims for stress disorders," Mar. 1988, Chartered Property and Casulaty Underwriter Journal, p. 12, Dialog: 00069691 File # 169.*

(List continued on next page.)

*Primary Examiner*—Joseph Thomas
*Assistant Examiner*—Carolyn Bleck

(57) ABSTRACT

A health care information management system uses a preexisting database of medical specialty claims, such as anesthesia claims, to profile the billing behavior of medical specialist providers, such as anesthesiologists. The software helps the user to determine which of the claims submitted by the providers are within accepted guidelines and industry standards. The software identifies providers who have submitted improper false claims. This is accomplished by comparing submitted claims with a database of histories of prior claims, as well as records of time accumulated data supplied by sources originating from hospitals, physicians and societies. The software incorporates unique triggers, which highlight those claims that indicate possible fraudulent submission. The system develops a profile of a provider's billing behavior and compares it to his peers. The software uses trigger filters to alert the insurance carrier if the provider's billing falls outside of a predetermined norm.

12 Claims, 12 Drawing Sheets

OTHER PUBLICATIONS

Finnegan, Daniel and Gail Simpson, "Winning the Fraud Game," Apr. 1992, Best's Review, vol. 92 No. 12, pp. 67–70, Dialog: 00608151/9 File # 15.*

Foppert, David, "Unveiling disability claims fraud," May 1992, Bests Review: Life/Health, p. 106, Dialog: 00128104/9 File # 169.*

Cox, Brian, "Computers key weapon in health care fraud battle," Feb. 8, 1993, National Underwriter: Property and Casualty/Risk and Benefits Management, p. 9, Dialog: 00141566/9 File #169.*

Friedman, Amy S., "Software helps expose claims fraud," Feb. 21, 1994, National Underwriter, vol. 98, No. 8, pp. 7 and 28, Dialog: 00827502/9 File # 15.*

"Cigna, IBM tech tool targets health care fraud," Oct. 3, 1994, National Underwriter Property and Casualty–Risk and Benefits Management, No. 40, p. 5, Dialog: 07545550/9, File # 148.*

Weisberg, Herbert I. and Thomas J. Marx, "Hamstrung adjusters need better ways to stop fraud," Sep. 1995, Best's Review, vol. 96, No. 5, pp. 90–94, Dialog: 01105301, File # 15.*

Baskerville, Ted, "Industry Fraud is on the rise; here's how to spot it," Sep. 1995, Best's Review, p. 96, Dialog: 00176038/9, File # 169.*

"Ferreting out fraudulent claims," Oct. 1998, Workers Compensation Monitor, p. 2, Dialog: 00201340/9, File #169.*

"Database Detectives", Nov. 1998, Insurance Networking, p. 24, Dialog: 02319921/9, File # 9.*

Barrett, Stephen M.D., "Insurance Fraud and Abuse: A Very Serious Problem," Aug. 16, 2000, access at www.quackwatch.org/02ConsumerProtection/insfraud.html, 5 pages.*

"Using Data mining to detect insurance fraud," 2000, access at www.spss.com, 9 pages.*

Luck, Ho Ming et al., HNC Software Inc, PCT US0021298, Detection of Insurance Premium Fraud or Abuse using a Predictive Software System, Dialog: 00779712/9 File # 349.*

Edelman, Susan et al, Rent—Doc, Jul. 16, 2000, 4 pages.

* cited by examiner

HCFA 1500

UB 92 HCFA 1450

CUSTOMERS SYSTEM APPLICATION

EXPANDED ARCHITECTURE
THE FOLLOWING DIAGRAM GIVES AN OVERVIEW OF THE CLAIMS ANALYSIS SYSTEM

TRIGGER I TIME DIFFERENCES

TRIGGER 2 MULTIPLE IDENTIFIERS

TRIGGER 3 UNBUNDLING

TRIGGER 4 UPCODING

TRIGGER 6 $3,000 THRESHOLD

TRIGGER 11 OUTPATIENT UNITS

HEALTH CARE BILLING MONITOR SYSTEM FOR DETECTING HEALTH CARE PROVIDER FRAUD

FIELD OF THE INVENTION

The present invention relates to the field of information systems for the use in reimbursement of medical provider billing, such as anesthesia billing, in regards to the detection, analysis and prevention of overbilling or fraud. It also allows for the development of profiles and utilizes a database relating to specific providers of medical care, such as anesthesiologists.

BACKGROUND OF THE INVENTION

Healthcare costs in the United States continue to rise because of a growing aging population, better education, new drugs and technology and greater healthcare benefits from the government as well as the insurance industry. Healthcare costs are over one trillion dollars a year with fraud and abuse representing about 10% to 15% of this. Conservative estimates put the cost of fraud to the country at over 100 billion dollars a year. The industry, as well as the government, recognizes this problem and have allocated manpower through the FBI and Department of Justice to crack down using the False Claims Act to prosecute these violators. But the discovery of the fraud is still a weak component both with the government as well as on the insurance industry's side.

At present, the federal government relies on personal informants, such as whistle blowers, for discovery, while the insurance industry relies on special investigation units, which are understaffed, lack the proper medical and accounting background and do not have the proper resources to discover where the false claims lie. In addition, the claims process is performed by employees called coders. They have no medical background, let alone have any exposure to medically arcane information such as anesthesia nomenclature. No one in the process of evaluating a claim submitted knows, for example, how to read an anesthesia chart. But the anesthesia chart is a blueprint for whatever billing is submitted by the anesthesiologist.

The head of fraud at insurance companies usually has a background in police work and because of limited medical knowledge, can neither decipher nor interpret technical medical practice information such as an anesthesia chart. Only the medical director of anesthesia, for example, can properly interpret and analyze an anesthesiologist's claim for payment but such proper and qualified anesthesiologist claim interpretations and analysis occurs currently in only 0.01% of anesthesiologist payment claims submitted.

Because of diminished reimbursements throughout the medical community, some doctor providers submit exaggerated billing claims so as to keep their revenue from declining. The software of the present invention is probative of fraud and is not merely an indicator of fraud. The software of the present invention uses a database comprising a history of over a million anesthesia claims to determine whether a particular claim being screened may be aberrant and therefore potentially fraudulent. Thereafter, the doctor in question who submitted the screened claim in question is profiled statistically to see how many standard deviations he or she is deviant generally in submitting claims as compared to his or her peers in regard to his or her pattern of claim billing. No other software process for detecting medical fraud has a built in database nor is any other software capable of addressing specific areas of specialty medical practice, which has triggers which are functionally data processing filters that operate as fraud flags built in to designate and recognize fraudulent bills submitted by medical providers, such as anesthesiologists.

Fraud detection and investigation with the utilization of the unique software of the present invention enables one to identify rapidly and accurately the abuse patterns specific to areas of medical specialty practice provider billing, such as anesthesia billing practices.

Once the software has identified abuse, the present invention commences a drill down process. Anomalous claims that are fraud-suspect are investigated and patterns of fraudulent billing from individual medical care providers are substantiated. This drill-down process, for anesthesisology, for example, utilizes more than sixty years of combined experience of anesthesiologists who detect what appears to the non-anesthesiologist to be subtle abuses but which nonetheless constitute patterns and practices of fraud and abuse in medical billing.

After identifying fraud-suspect aberrations of submitted claims, a proven state of the art recover process takes place using professional staff. This unique recovery process includes a medical provider, such as an anesthesiologist, addressing specific billing issues with the anesthesia provider who submitted fraud-suspect bills. Therefore, the present invention eliminates the arcane nomenclature, confusion and the involvement of three or four layers of non-knowledgeable insurance personnel who lack the requisite skill to analyze even rudimentary medical records, let alone such sophisticated and thus obfuscated and arcane material as anesthesia records.

Among related patents which describe attempts to monitor medical provider billing while preventing fraudulent billing include U.S. Pat. No. 5,995,937 of DeBusk.

DeBusk '937 describes a method of structuring software for creating a health care information management system. In contrast to DeBusk '937, in the present invention the use of software and expert consultants is used to screen health care billing claims to flag possible fraud for further investigation.

However, DeBusk '937 uses the notions of NODE, MODULE, CONTAINER, RESOURCE AND DATA to describe its software system. In FIG. 2 it uses a "clinical pathway" example which shows how an anesthesiologist fits in. DeBusk's examples of fraud relate more to inventory control of supplies in hospitals than the data processing comparison of hospital records with physician payment claim records to flag inconsistencies where there should not be any, which is one of the linchpins of the present invention. The last paragraph of DeBusk '937 claim 6 which states "analyzing the utilization study module . . . " relates to detecting trends in health care data.

U.S. Pat. No. 6,070,141 of Houvener basically deals with assessing the quality of an identification transaction in an effort to limit identity-based fraud during on-line transactions, which is vastly different from the present invention. It does create a database of "quality score assignments" that are distinguished from the data processing fraud flag filters that are the triggers of the present invention. Houvener '141 uses quality indicators to determine the level of scrutiny. It adjusts historical data as a function of transaction data, which is also used in many commercial applications and is closely related to surveys and polls.

U.S. Pat. No. 5,991,758 of Ellard involves a system and method for indexing information about entities from different information sources. In this way, an entity may be related to records in one or more databases. While the abstract objective of Ellard '758 bears some relation to comparing hospital billing records to those of a physician, the methods used are different from those of the present invention. Ellard '758 uses the notion of a master entity index, MEI. Ellard '758 uses the addition of confidence levels for matching attributes to compare to a threshold level for selecting data records for display, which may be construed as data processing filter triggers.

Moreover, U.S. Pat. No. 6,058,380 of Anderson describes a system for processing financial invoices for billing errors. Anderson '380 describes in Table 3 therein the use of "reasonability" criteria and historical data to determine if billing errors have occurred.

Additionally, the *New York Post*, Jul. 16, 2000 edition, reports as its leading article on page 1 an article entitled "Rent-A-Doc: MD's lease their names to front for medical mills" about medical providers using a multiplicity of entities with different addresses to boost billing.

Currently, these major problems exist because the insurance industry separates their claims departments for handling hospital claims from the physician claims, so that they are unable to discover the situations disclosed in the *New York Post* article.

OBJECTS OF THE INVENTION

Therefore an object of the present invention is to provide a system which monitors medical provider billing to prevent fraud.

An applications object of the present invention is to selectively manage a user defined, user configurable database that is provided from standardized resources. In contrast to the present invention, at the current time, upon receipt of a claim by the payer, there is little to guide the claim processor in order to identify a claim being one that should be paid or one that should be investigated. Therefore, an object of the present invention is to institute several triggers, which are data processing filters capable of flagging fraud-suspect data in a medical provider claim for payment. The triggers interface with the information provided in the claim itself.

In addition, the present invention recognizes that there is a need to stop improper provider billing in medicine, in regard to preventing overpayments that are normally processed by the payers. The system of the present invention processes the information at a rate that allows the payer to effectively keep up its commitments while assuring that overpayments no longer occur.

At the present time, medical providers submit claims separately from the medical institutions, such as hospitals. The providers file claims for payment on a standardized 92UB1450 form whereas the hospitals use the standardized HCFA 1500 form. These two forms are submitted either by electronic or paper filing to respective claims departments of the insurance carrier payers. However, neither these two forms nor the data they contain even interface with each other, nor are their combined data evaluated side by side by the same insurance company coder to see if there are any inconsistencies.

Therefore it is also an object of the present invention to provide a proprietary fraud-preventive system of analysis of medical provider payment claims which allows the claim processor to take the data from the pertinent fields from each respective claim form and compare them for any discrepancies beyond allowable circumstances.

By comparing the fields, such as #24D or 24G in the HCFA 1500 form with the fields such as #710 and #370 respectively in the 92UB1450 forms, the present invention probatively determines if overbilling and/or patterns of fraud have occurred.

With the data provided by these claims, it is also an object of the present invention to be able to generate specific profiles pertaining to an individual provider's billing habits. This enables the insurance company payers to be able to identify those providers that have submitted false claims, which, hence, drive up the cost of health care for the country.

The present invention has an advantage of not being biased, because it utilizes a huge historical reference database of previous claims to ensure accuracy and validation of data processing using the fraud filters of this invention. In addition, in the specialty medical field of anesthesia billing is performed as a taxi cab driver bills his fare, i.e., there is an initial charge and then the calculation of time per unit. The software of the present invention and overall solutions hold the biller accountable to a reasonable time frame by constructing the following preventive claims processing structure.

It is also yet another object of the present invention to improve over the disadvantages of the prior art.

SUMMARY OF THE INVENTION

The present invention is a health care fraud-detection information management system that uses a pre-existing database of medical specialty claims, such as anesthesia claims, to profile the billing behavior of medical specialist providers, such as anesthesiologists. The software helps the user to determine which of the claims submitted by the providers are within accepted guidelines and industry standards. The information management system allows for the creation by the user of software objects representative of specific events and/or resources, which occur during health care rendition, such as the administration of anesthesia to the patient.

For example, presently, anesthesia claims are processed by insurance carrier coders who have no medical knowledge foundation to interpret these claims. In contrast, the software of the present invention relies on data processing filters developed with anesthesiologist skill and therefore, since the filters "know what to look for" identifies providers who have submitted improper false claims. This is accomplished by the software that compares a submitted claim with the reference database of the present invention as well as the reference data accumulated data over time supplied by sources originating from hospitals, physicians and professional societies. Unlike any other software, the present system is probative for each and every screened claim. The analysis provided by the present invention is thus more than a mere indicator that functions by comparing billing practices on the basis of differences quantified by statistical standard deviations.

At the core of the application of the present invention are nine unique triggers that respectively comprise data processing filters for flagging fraud-suspect data within claims submitted for payment by health care providers. The triggers, or data processing filters, are described below. The software application was created using spreadsheet software, such as that developed by Hyperion, Inc. and known as Essbase software.

The information management system includes:

1. a computer system
2. a display 3. a storage
4. a processor
5. an input means
6. operating and analytical software
7. a database of historically relevant comparative data Specifically, the software of the present invention utilizes triggers which highlight those claims that indicate possible fraudulent submission.

In contrast to the presently existing accounting systems, the system of the present invention combines the claims off of the 92UB1450 form submitted by the hospital, with the HCFA 1500 form submitted by the health care (e.g., doctor, such as an anesthesiologist). The code fields in question that are examined are 24D on the HCFA form if the claim was submitted to an insurance company or field number 24G if the claim was for a federally funded Medicare patient. These fields are compared to fields 710 and 370 -on the hospitals insurance claims form. At times, these fields are not complete, therefore, part of the system includes requiring any claim submission by the hospital to have time units recorded in field 710 or field 370 in column 42 (REV CO.) of the 92UB1450 form. These time units are recorded by either the recovery room nurse pertaining to field 710, or by the operating room nurse pertaining to code number 370. If either of these times have fifteen minute's difference between them and the provider's times, such as the anesthesiologist times, then the claim will be labeled suspicious and a drill down process occurs using the physician's other prior claims. The system then determines if this is a pattern of behavior on the part of the individual provider for improperly reporting time, or whether this was the rare case that the patient needed to have extra time for the anesthesiologist to tend to his well being.

This time comparison procedure adds full accountability to the anesthesiologists' claim that the procedure, which was billed, was accurate. If not for the process and software of the present invention, a provider such as the anesthesiologist can submit fabricated and inflated times, thereby raising the rates in his bill to the insurance company.

In addition to comparing the anesthesiologists' HCFA 1500 form to the hospitals' 92UB1450 submission, the system of the present invention compares the surgeons' HCFA 1500 form submitted for the same patient. By comparing data from the surgeon's HCFA 1500 with data from the same form submitted by an anesthesiologist, the system identifies and thus deters a process of fraudulent upcoding. Upcoding is a way for an anesthesiologist or other health care provider to fraudulently fabricate an inflated payment claim in a manner presently very difficult to detect by ascribing a higher time unit value to a case than that which the surgeon gives for the same patient in the same surgical operation at the same time and place. The fraud detection method of the present invention compares, for example, the anesthesiologist claimed codes listed in field #21 on the HCFA form with those claimed by the surgeon for the same surgical operation on the same patient at the same time and place.

Anesthesia is a unique specialty in that it is the only specialty in medicine that is reimbursed by time units. Up until now, neither the insurance industry, the government, hospital nor the patient themselves, had any idea if the time units that were submitted were accurate. Now, by using the software of the present invention in conjunction with its preventive business model for stopping fraud, a compliance committee, an insurance company and the government, can get an accurate account for an anesthesiologists, claim. The system develops a profile of a provider's billing behavior and compares it to his peers. In addition, the software is probative because it has a set value to each and every time submitted.

The software uses triggers to alert the insurance carrier if the provider's billing falls outside of a predetermined norm. While other data processing filter triggers may be used to flag fraud-suspect data, the following triggers, or data processing filters that generate fraud flags, are illustrative.

Trigger 1

Time Differences:

Anesthesiologists bill by unit value concerning the surgical procedure plus the time units. Standard time units are broken up into 15-minute intervals. Therefore, every 15 minutes that the anesthesiologist works is equal to one unit in value. The software fraud detection system of the present invention holds the anesthesiologist accountable by comparing his or her claim to the submission of times listed on the 92UB1450 form listed in field #370 and #710. These can be found under #42 REV CO. for the hospital billing form. Fields 24D and 24G of the HCFA 1500 form submitted by the anesthesiologists, for example, are compared. Any difference in times greater than a pre-selected amount results in the software generating a fraud flag for scrutiny and examination of a possibly fraudulent payment claim.

This can be stated as follows:

$A$=Start time (Anesthesiologist)−Start time (Hospital=# minutes $B$=End time (Anesthesiologist)−End time (Hospital)=# minutes Total Minutes=$A+B$ Each 15-minute interval is then converted into 1 unit and billed as a unit. Times recorded by the hospital are start time that is when the patient comes into the operating room and end time when the anesthesiologist leaves the patient's side in the recovery room. Deviation values are then calculated based on the deviation table below:

a. >20 minutes−1 standard deviation b. >45 minutes−2 standard deviations

C. >50 minutes−3 standard deviations d. >65 minutes−4 standard deviations

By holding the anesthesiologist accountable for his or her submission of times, the insurance industry prevents creation of time and false claims are recognized.

In addition, the software of the present invention has an existing database which compares the time units billed by the provider, such as an anesthesiologist, to the same procedure billed by many other similar providers, such as anesthesiologists.

Trigger 2

Multiple Identifiers for Participators:

Within all insurance companies as well as Medicare, some physicians are participators and some are non-participators. The participators sign a contract to bill the particular payer at a set and reduced rate. Often a physician although contractually obligated to bill the reduced participator rate will bill the increased rate of a non-participator. The software of the present invention identifies these abusers by cross-referencing Tax I.D. numbers, different addresses used by participators, Medicare numbers and identifying at which hospital they performed the procedure. Most teaching hospitals have contractual obligations with Insurance Companies and doctors there typically are participators. As participators bound by contracts, doctors should not be able to attempt to fraudulently collect inflated payments for which they are ineligible by billing a non-participator (i.e., higher) rate. In some instances, some physicians can have more than one job or address and manipulate the system by also using another Tax I.D. or, billing in the name of another corporation. All of these abuses are exposed by the software of the present invention by comparing the health care providers non-varying identifying information, such as a Medicare number, with the name and address of a health care provider on a claim submitted for payment. Such a comparison will expose, for example, a particular anesthesiologist who bills a paying insurance carrier under multiple entity names and thereby confuses and obfuscates his/her real identity as presented to the payer, and at the same time obfuscates his/her true identity to the payer with the present result that payers are helpless to determine which individual medical care providers are improperly and fraudulently billing multiple rates for the same procedure by using multiple identities and thus purporting to be more than one provider for the simple reason that they presently know they can't get caught.

Trigger 3

Unbundling:

A common avenue for fraudulent bill inflation is for a doctor to unbundle his/her billing. Unbundling is the practice of taking one event of medical care rendition or one surgical procedure, for example, that should be billed under one code and billing a number of codes derived from that one procedure. For example, if a woman has an epidural for labor pain, but must deliver the baby by cesarean section, an anesthesiologist who unbundles his/her billing may bill individual unbundled codes for:

1. Labor Pain
2. Cesarean Section
3. Laryngoscopy
4. Intubation
5. Gastro Tube Insertion In the above example, only Number 2, Cesarean Section, should probably be billed, the remaining above codes being procedures that should normally encompass the service of a Cesarean Section.

Another example of unbundling from a different area of health care rendition concerns pain management where a single office visit can fraudulently generate several different bills for one diagnostic work-up, as well as treatment of several different segments of the body. A separate trigger for pain management unbundling is described below because the unbundling practice is so frequently encountered in pain management.

The unbundling trigger of the present invention thus alerts the user of the software of the present invention as to any patient who has had more than one procedure performed on them in the same day or same event-day where treatment may have begun before midnight and ended after midnight in a single continuous treatment session. Obviously, there are some occasions when patients legitimately need to return to the operating room and those cases are accepted as fair billing practices.

Trigger 4

Upcoding:

Another method that anesthesiologists use to inflate the price of the bill is called upcoding. This includes recording a fraudulent CPT Code (current procedure terminology that the surgeon uses to evaluate the procedure of the surgery performed), and by so doing, the provider (e.g., an anesthesiologist) can be compensated more than if he/she had recorded a legitimate CPT code on a payment claim for performing the case. The anesthesiologist must place the same CPT Code on the HCFA 1500 form as the surgeon, otherwise, it should be suspected as fraudulent upcoding. For example, if a surgeon designates as a Sigmoidoscopy as having been performed but the anesthesiologist records a CPT Code reflecting a Colonoscopy, which a similar but more extensive and more expensive procedure, the upcoding anesthesiologist will overbill the payer anywhere from two to three hundred Dollars. Such practices occur because the upcoding anesthesiologist cannot get caught by claim examiners who do not have the knowledge or computer resources to compare the surgeon-reported data with the anesthesiologist's claims. This invention solves that claim-examining problem. In this case of the Upcoding trigger as applied to the medical specialty of, for example, anesthesiology, this invention solves the payer claim examining problem by specifically monitoring section 24D on the HCFA 1500 form of both the surgeon and the anesthesiologist, the present invention exposes upcoding.

Trigger 5

Profiling Modifiers:

Besides unit value of a procedure, and time units, anesthesiologists also bill using modifiers. These include the following:

1. insertion of an arterial line
2. central venous pressure monitor
3. utilization of controlled hypotension
4. emergency
5. American Society of Anesthesiologists (ASA) evaluation upgrade Furthermore, the anesthesiologist places a risk value to every patient undergoing anesthesia;

P1—normal patient

P2—patient with mild systemic disease

P3—patient with severe systemic disease

P4—patient that is in a constant threat to losing their life

P5—moribund patient not expected to survive 24 hours

If the anesthesiologist designates that the patient is evaluated at a P3–P5, he/she can charge an extra $100.00 to $300.00 dollars for performing the procedure.

The database that is installed into the software of the present invention gives the percentages of cases that are evaluated at P3–P5, as well as those that need the extra monitoring. By profiling the anesthesiologists, it is able to determine if any are billing abusing, placing unnecessary monitoring or placing higher risk values to patients so they collect larger fees.

Specifically, for example, if it is established over a long time, over a large geographic area or nationally, and over many JCAH (Joint Commission on Accreditation of Health Care Facilities) accredited institutions by statistically significant data that, for example, 3% of surgical patient's are legitimately coded as risk category P3 but a particular anesthesiologist routinely codes all his/her patients as P3 it is beyond peradventure that said anesthesiologist is using the P3 designation fraudulently to get a larger paycheck from the insurance carriers to which payment claims are submitted.

Trigger 6

$3,000 Threshold:

It is a standard in the industry for the anesthesiologist to be paid anywhere from one quarter to one third of what the surgeon is paid. It is highly unusual and aberrant for the anesthesiologist to be paid more than the surgeon.

The trigger here is to take every bill that exceeds a predetermined amount, preferably $3,000.00 at the time of this invention, analyze it to make sure it is not over billed and does not exceed the payments due the surgeon of the case.

In cases where the anesthesiologist's bill does exceed the predetermined trigger amount, an additional calculation will be made comparing the anesthesiologist's bill to that of the surgeon. When the bill ratio for anesthesiologist: surgeon exceeds about 1:3 a fraud flag for further scrutiny will be generated by the present invention.

Trigger 7

Outpatient Units:

Outpatient settings are any procedure not performed in a J.C.A.H. (Joint Commission on Accreditation of Health Care Facilities) accredited facility (e.g., hospital). Rendering health care in a non-JCAH facility may be in a doctor's office or in an outpatient surgical setting. This creates many opportunities for billing irregularities because the controls outside of a JCAH accredited facility are few. There is no accounting for time and because of the types of procedures performed in these non-JCAH settings, an anesthesiologist can render service to several patients in a short period of time but yet, bill hours for each case. Here again, the database of the present invention comes into play. When a bill is submitted a fraud flag is generated when the software determines that a procedure took place outside of a JCAH accredited facility, because within a JCAH facility there are fixed time limits are normally placed on reimbursements schedules.

Therefore, for example, if a Colonoscopy was billed six 15-minute time units for 1½ hours and the database shows that 80% of Colonoscopies are performed within thirty minutes, then the payer need only to reimburse two 15-minute units for time rather than the billed six units.

Box 24B corresponds to location of surgical procedure field 11 shows an office procedure while field 24 shows that the procedure took place in an out patient surgical center. Because of the lack of controls there may be many more false claims filed from these non-JCAH facilities than JCAH accredited hospital based practice. Here too, the system applies a fair reimbursement data processing filter of a ratio of anesthesiologist to surgeon billing of about 1:3, or roughly at thirty percent of the surgical bill.

Trigger 8

Pain Management Unbundling:

Pain management is frequently a problem area where fraudulent over-billing is encountered by payer insurance carriers. General medical billing Unbundling, as in Trigger 3, is so frequently encountered in the pain management specialty area that pain management unbundling requires its own separate fraud-flag trigger.

In pain management, for example, a sympathetic block of the lumbar region can include the following charges.

1. X-rays of the spine
2. Fluoroscopy of the spine
3. Local anesthesia
4. Insertion of needle
5. Injection of steroids
6. Sedation of the patient
7. Then multiple charges per each segment These bills should be paid by the procedure itself and not be allowed to be unbundled. Codes that will be scrutinized to find evidence of pain management unbundling are the following:

20550—Trigger point injections

64520—Lumbar nerve block

62284—Myelogram

64440—Paravertebral nerve block

62289 Lumbar epidural

A fraud-flag will be generated by the present invention where pain management unbundling occurs as a pattern and practice of the billing of particular health care providers, when claims from such individuals are compared to other claims having been presented in the past by the same individuals.

Trigger 9

No Fault/Disability:

The amount of medical fraud in regard to no fault automobile insurance as well as disability insurance is believed to be at epidemic levels. Apparently, there are neurologists, chiropractors and pain specialists whose practices thrive on producing large bills with complicated diagnoses, which allegedly help their patients inflate damages for pain in suffering lawsuits. Presently, the insurance industry does not do an effective job of profiling the physicians involved with the diagnosis and treatment for purposes of fraud detection and prevention. Each case itself may stand on its own merit but when a chiropractor is profiled and it is shown that he or she has given the same diagnosis and treatment schedule to hundreds of different patients then the proper investigational work-up will begin. The system of the present invention assists the insurance company with insight, interviews and opinions which their resources may have trouble accomplishing.

The no-fault/disability trigger is a data processing filter that examines multiple claims of a given provider for a pattern of repetitive diagnosing of the same injuries or patient conditions and flagging the provider as a possible fraud feasor and the repeatedly diagnosed injury or condition as one that lends itself to fraudulent abuse.

BRIEF DESCRIPTION OF THE FIGURES

The present invention can best be understood in connection with the accompanying drawings, in which:

FIG. 12 is a Flow chart of a Trigger 8 identifying claims submitted in the field of Pain Management; and.

DETAILED DESCRIPTION OF THE PREFERRED EMBODIMENT

In the following description, the anesthesiologist example is used; however, similar structures relating to other medical specialists also apply.

Figure 1:
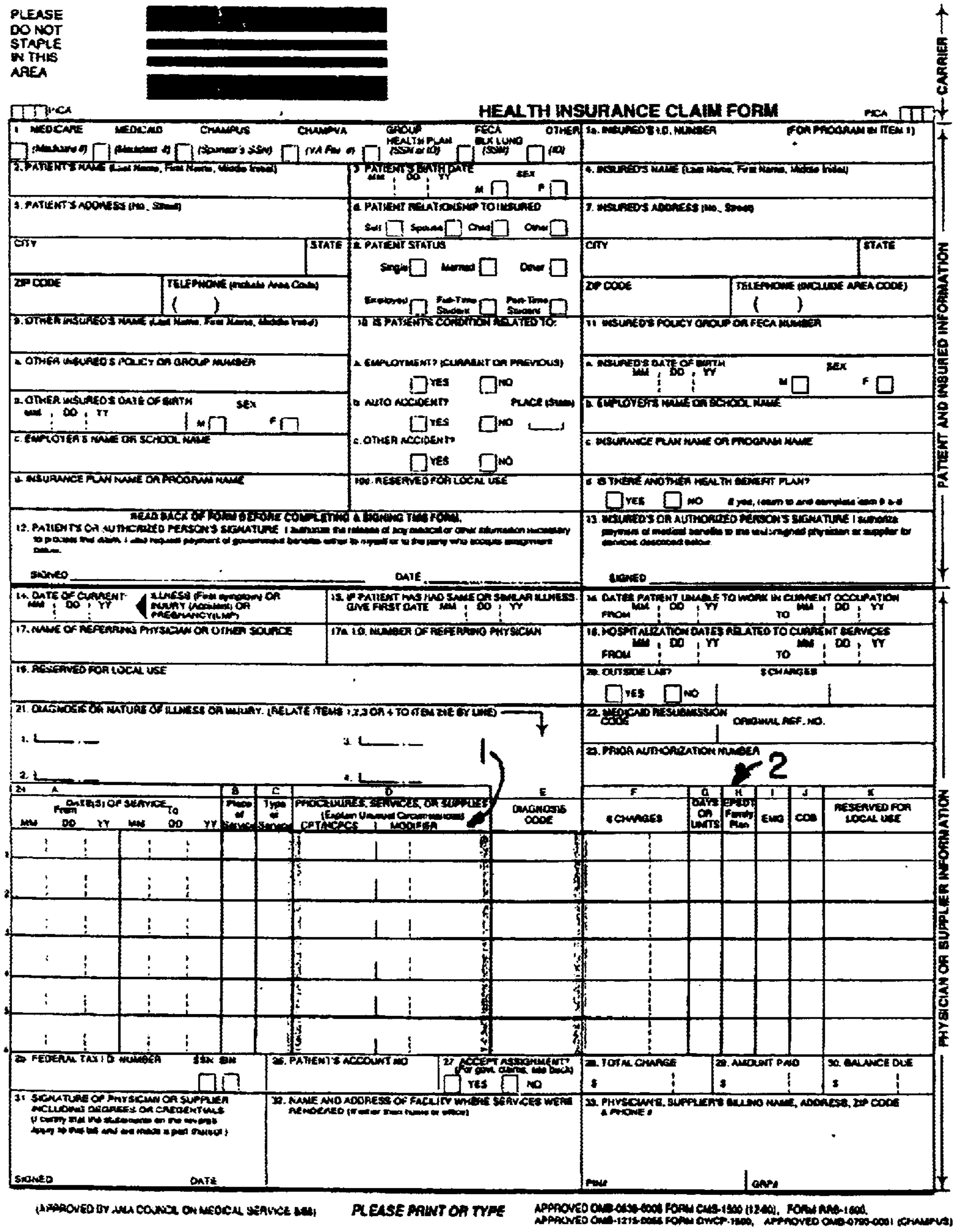
FIG. 1 is a Form HCFA 1500 for health care provider used in connection with the system of the present invention.

FIG. 1 shows a HCFA 1500 form as used by providers for health insurance claims. Column 24D 1 records the starting and ending time of a procedure. Column 24G 2 records days or units (15 minute periods).

Figure 2:
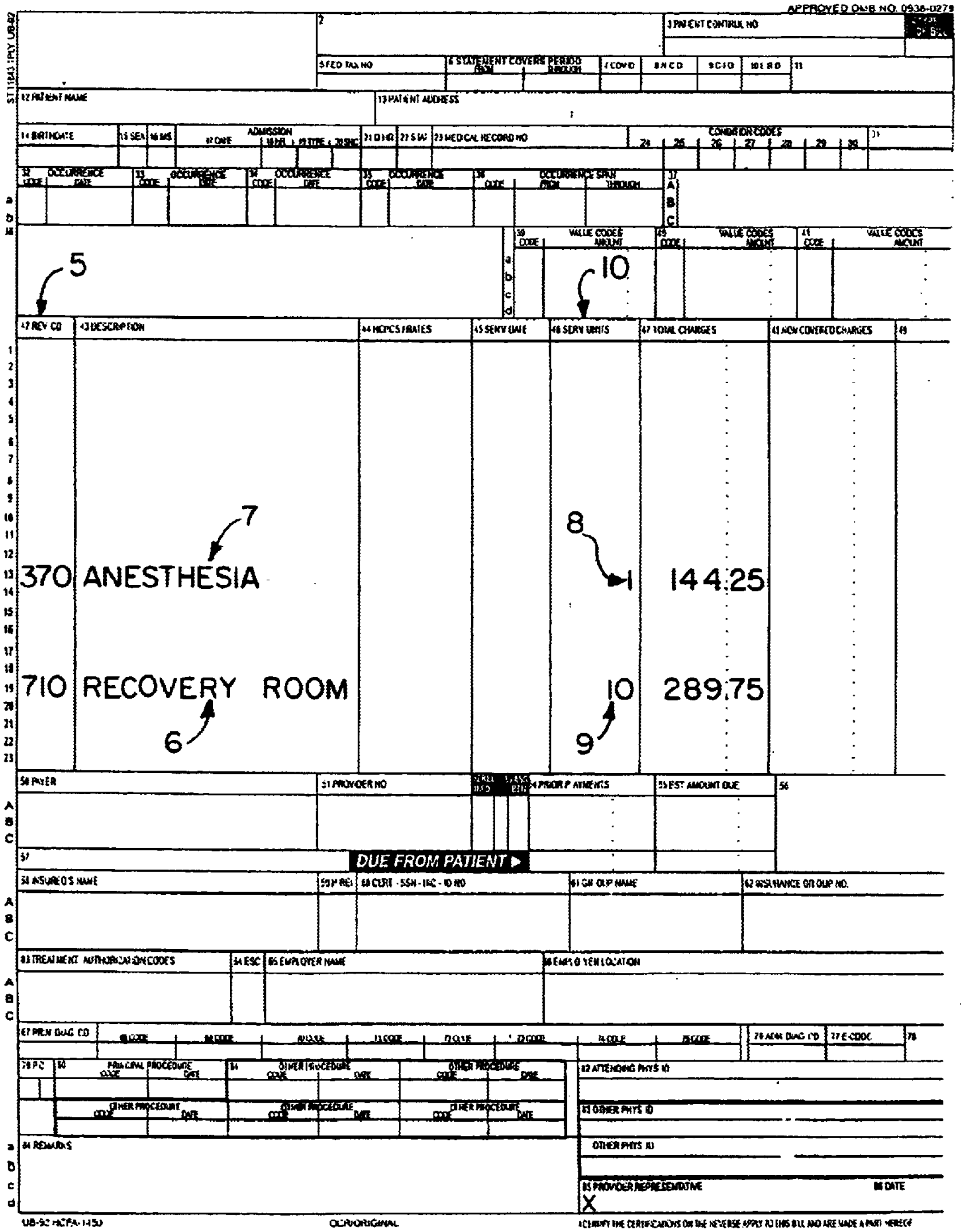
FIG. 2 is a Hospital form UB 92 HCFA 1450 for health care procedure used in connection with the system of the present invention.

FIG. 2 shows a UB92 HCFA 1450 form commonly used by hospitals to record information about patient medical procedures. Column 42 5 lists the procedure codes which are described in the next column with entries such as 370 anesthesia 7 or code 710 recovery room 6. The service units are shown in column 46 10 with entries such as 1 8 and 10 9 representing time units in 15 minute periods.

The software databases from various sources include coded versions of the previous two forms shown in FIGS. 1 and 2 along with other procedure-specific and historical data.

Figure 3:
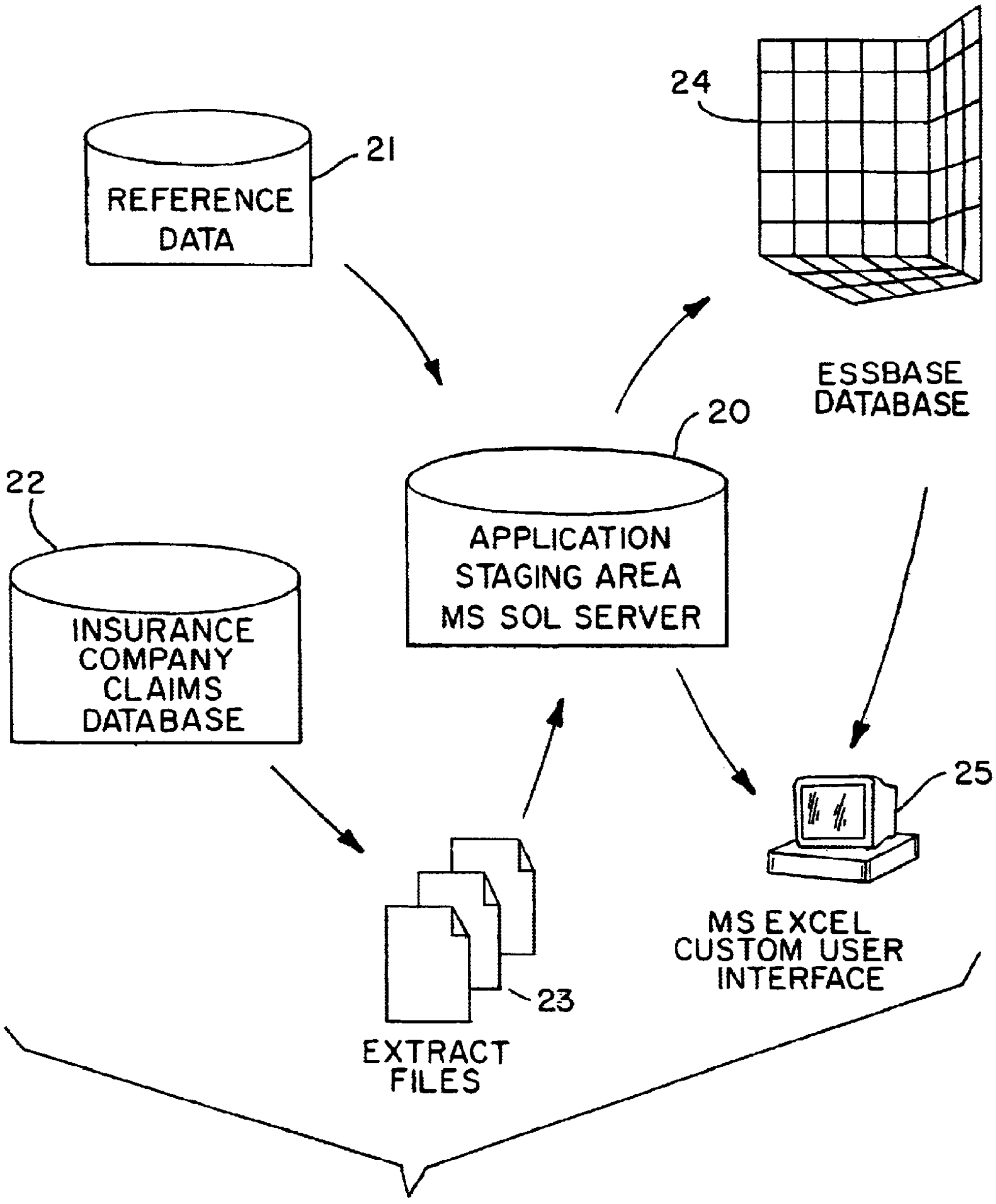
FIG. 3 is a Overall software system of the present invention.
Figure 4:
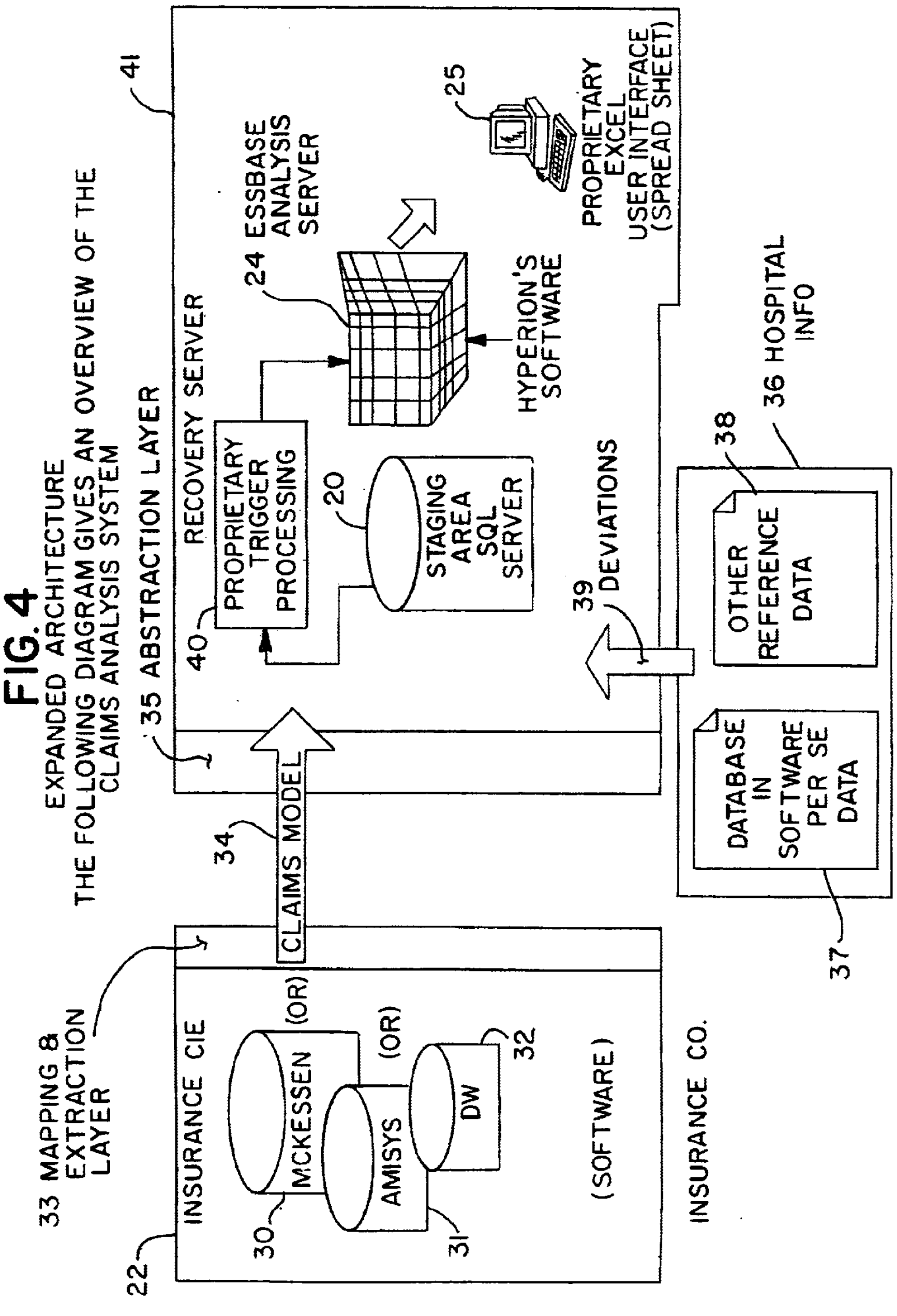
FIG. 4 is a Block diagram of software modules thereof.

The overall software system of FIG. 3 and the more detailed block diagram of FIG. 4 show the relations among the various modules.

For example, as shown in FIG. 3, files 23 are extracted from insurance company databases 22 and are brought to the application staging area 20 which can be implemented as a MICROSOFT® MS SQL® Server. Reference data 21 is also brought in. Both the Custom User Interface 25 written in a spreadsheet type package as well as the ESSBASE® Database 24 constructed for specific end user applications receive data from the Staging Area 20.

In FIG. 4, the insurance database is further broken down as one or more of a MCKESSON® 30, AMISYS 31 or DW 32 databases. A Mapping and Extraction Layer 33 interfaces with a Claims Model 34 to provide the required data through Extraction Layer 35 to Recovery Server 41. Hospital Information 36 consisting of Per Se Data 37 and Other Reference Data 38 are brought in via Deviations portal 39 to Recovery Server 41. The latter consists of the Staging Area 20, the Essbase Server 24 and a special Proprietary Trigger Processor 40. Final User analysis is performed on the User Interface 25.

FIGS. 5 through 13 present high level flow charts of the various triggers which flag claims for further scrutiny.

Trigger 1, Time Differences, shows how data from two forms are compared to record from 1 to 4 deviations in time between that recorded by the specialist and the hospital.

Trigger 2, Multiple Identifiers, is used to screen for doctors or specialists who use multiple identifiers to skirt proper system identification.

Trigger 3, Unbundling, attempts to identify cases where claims should be coded as a single procedure which usually results in lower approved charges.

Trigger 4, Upcoding, is invoked when the procedures are coded differently by the specialist and the surgeon.

Trigger 5, Profiling Modifiers, relates to extra-cost modifiers or patient risk categories; these are related to accumulated database numbers with excess charges being flagged.

Trigger 6, for claims in excess of $3000, flags all claims exceeding $3000 (or any other fixed figure) and fetches a corresponding surgeon bill for comparison.

Trigger 7, Outpatient Units, flags all outpatient claims and retrieves other data which may brand seemingly excessive claims.

Trigger 8, Pain Management, keys on specific pain management codes and then fetches procedure description which determine if the pain management is included in the procedure.

Finally, Trigger 9, No fault/Disability flags all such claims of this type. A profile database entry for the physician or other practitioner identified on the claim is fetched if available to shed some light on the frequency and amount of the present claim as related to history. If no profile database entry exists, one is started for the practitioner, otherwise the existing historical data is updated by the present claim data.

Operation Of The System Of The Present Invention

The data processing system of the present invention detects health care provider fraud. It includes a computer processor for processing data, a computer storage database for storing data on a storage medium, an initializer for initializing the storage medium and a second processor for processing data regarding payment claims submitted by health care providers to payers.

The software of the present invention may be used by remote input at a source computer of payment claim data. Remote users may then transmit the claim data to a central processing computer located elsewhere by any effective data communications means, such as fiber optic cable, telephone line, micro wave transmission or a world wide communication interconnection web such as an internet. The processed data, with flags having been generated, may then be communicated back to the remote user in visually displayable form, printable form, computer storable and computer readable form, or any other form in which data may be usefully handled.

The payment claim data is processed to identify and flag fraud-suspect inconsistencies and anomalies regarding payments claims submitted for payment by health care providers. Internal inconsistencies are those found within a single claim arising from a single patient procedure done at a given time and place, e.g. the anesthesiologist billed four units=120 minutes for a procedure that the hospital OR reported as having been 60 minutes, for the same patient, same hospital, one the same date.

External inconsistencies are those found between a single claim arising from a single patient procedure done at a given time and place, and claims of the same general type taken from a reference database for comparison to the claim under review, the same general type meaning a large statistically significant stored reference data base of claims submitted by the same type of health care provider e.g. a reference databases from one or a consortium of insurance carriers of anesthesiologist billing for anesthesia administered in connection with a given surgical procedure so that a statistically significant deviation of, for example, 1.5 or more standard deviations from the norm in a claim under review will trigger a fraud flag because the claim under review is one where the anesthesiologist billed excessive time (by 1.5 or more standard deviations) as compared to the normal amount of time expected on the anesthesiologist's bill as determined by the insurance carrier database of a large number of anesthesiology claims connected with the very same kind of surgical procedure.

In effect the reference database provides data that informs, or calibrates, each of the triggers with baseline information against which each trigger (data processing filter) compares (i.e., screens for fraud) data from individual claims being submitted for payment by health care providers The calibration of the data processing filters (triggers) by using reference data in the present invention provides, for example, for the trigger filters, and the human claims examiner, the information that constitutes the statistically normal time that is billed by an anesthesiologist for a given procedure. Such a norm is derived from a reference data base, the norm being applied to calibrate, or set-up internal the expectations contained within the fraud-flag data processing trigger filter and upon which the fraud-flag trigger filter operates.

The present invention provides a data processing filter means that enables insurance carrier claim payers to fraud-profile of individual health providers based on an accumulated history of claims submitted by an individual health care provider.

In fraud profiling the present invention accumulates history of discrete data representing claims submitted for payment by an individual health care provider and subjects the data and claim history to one or more profiling modifier fraud-flag data processing trigger filters, which identify and point out inconsistencies between the accumulated claim submission history of the individual provider, when those data are compared to the normative health care parameters for the same medical care events and procedures derived from statistical normative data.

An initializer inputs, displays, retrieves, processes, compares, filters and stores data on the storage medium of individual health care provider payment claims data.

The calibrator retrieves and analyzes reference data regarding health care procedure billing parameters, wherein the billing parameters data are furnished from health care industry, insurance industry, and/or governmental health care insurance payer information data bases, such as insurance company claims database(s) and hospital/professional medicine practitioner statistical data on time requirements for specific medical procedures, normal time durations and billing amounts connected with specific medical procedures.

Figure 5:
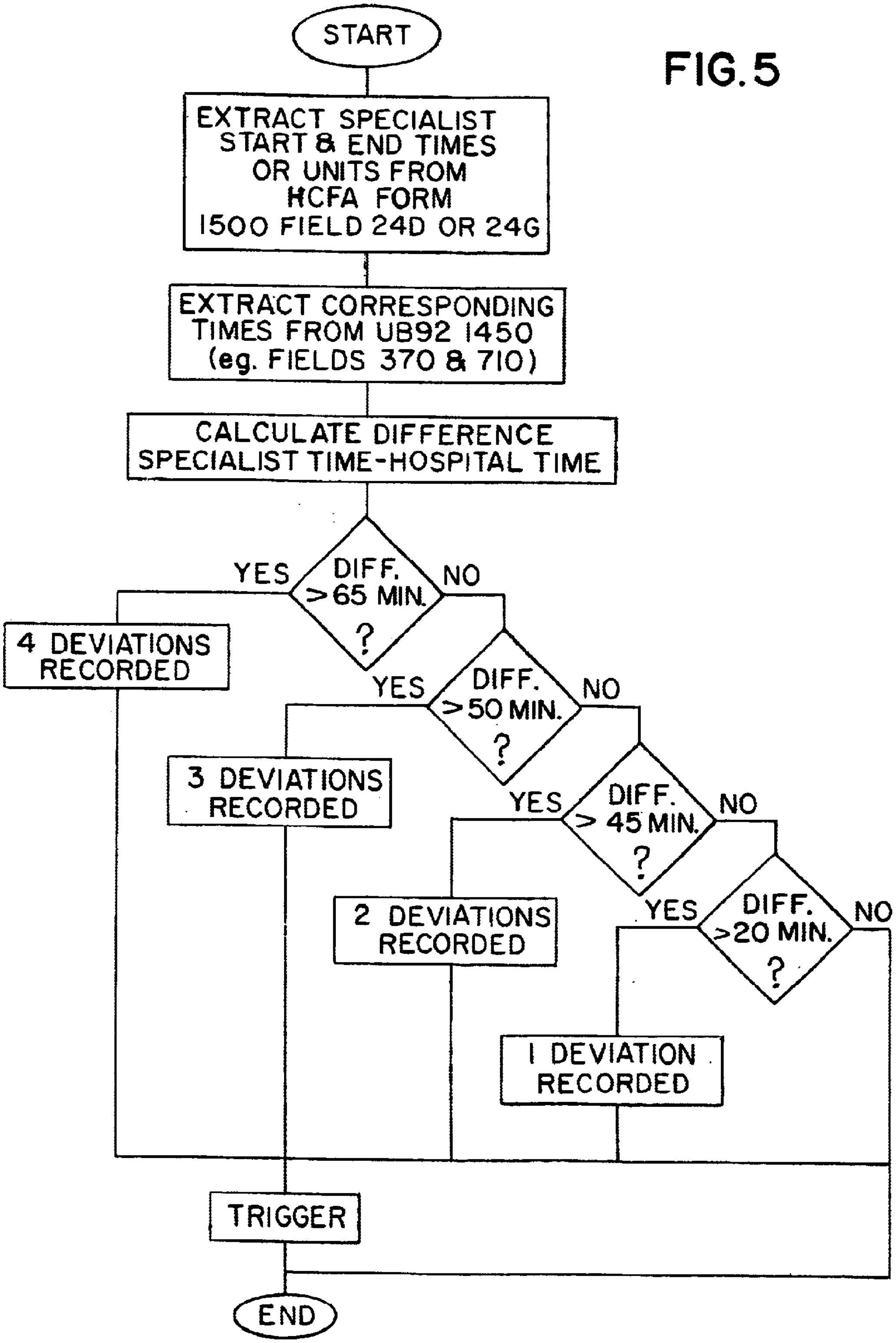
FIG. 5 is a Flow chart of a Trigger 1 identifying Time Differences.
Figure 6:
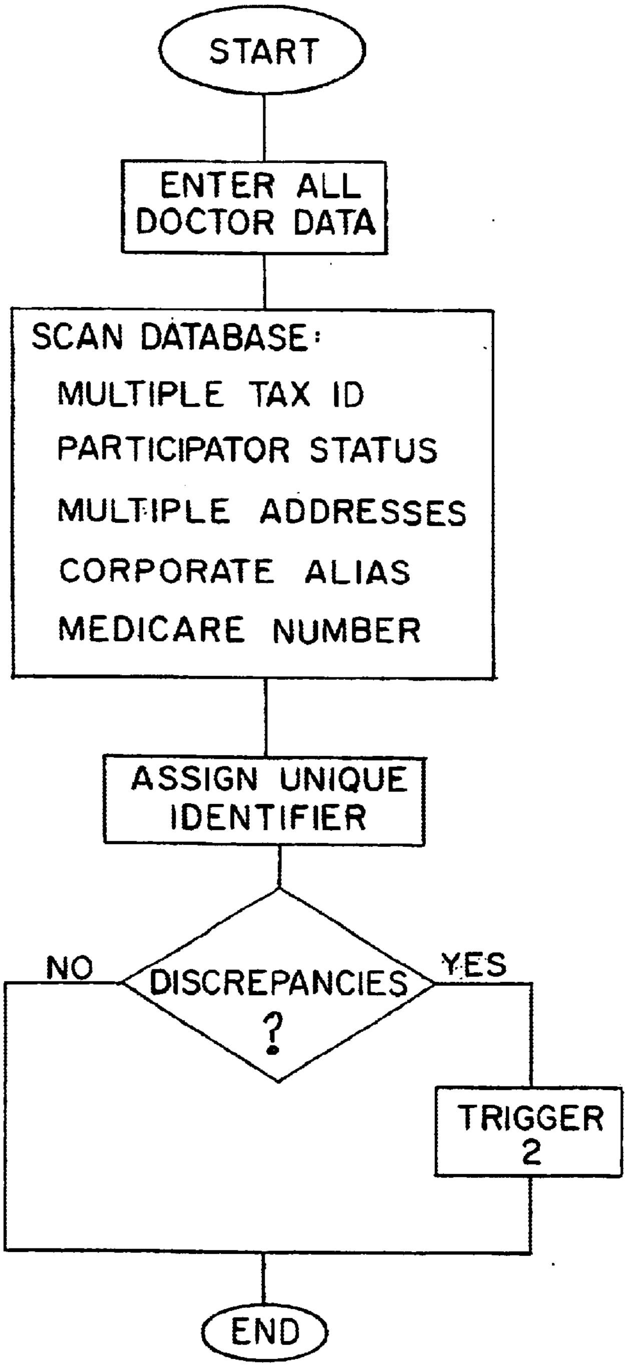
FIG. 6 is a Flow chart of a Trigger 2 identifying Multiple Identifiers.

One of the fraud-flag data processing trigger filters, identified as Trigger 1 in FIG. 5 herein, is a time-difference flag generated in response to a predetermined calibration threshold, when the time duration reported on a payment claim by an individual health care provider for a patient care event is compared to an independently recorded measurement of the same time duration as reported by a hospital or other health care provider.

Still another fraud-flag data processing trigger filter, identified as Trigger 2 shown in FIG. 2 herein, further compares the individual information identifying particular to health care providers with payment claims submitted by other health care providers having different addresses and different business entity names, such as described in the *New York Post* article in the Background of the Invention herein, to determine if the same health care provider as identified by a never-varying Medicare provider number has submitted claims for payment for health care provided to patients under an improperly and superficial multiplicity of names and/or addresses. This trigger filter locates multiple claim providers that submit a multiplicity of providers to simultaneously be both a participant medical care provider and a non-participant provider under a particular contractual scheme of reimbursement, that fraudulently appear to the payer to entitlement to differing reimbursement rates by virtue of the improper multiplicity of claimed health care provider identities.

Figure 7:
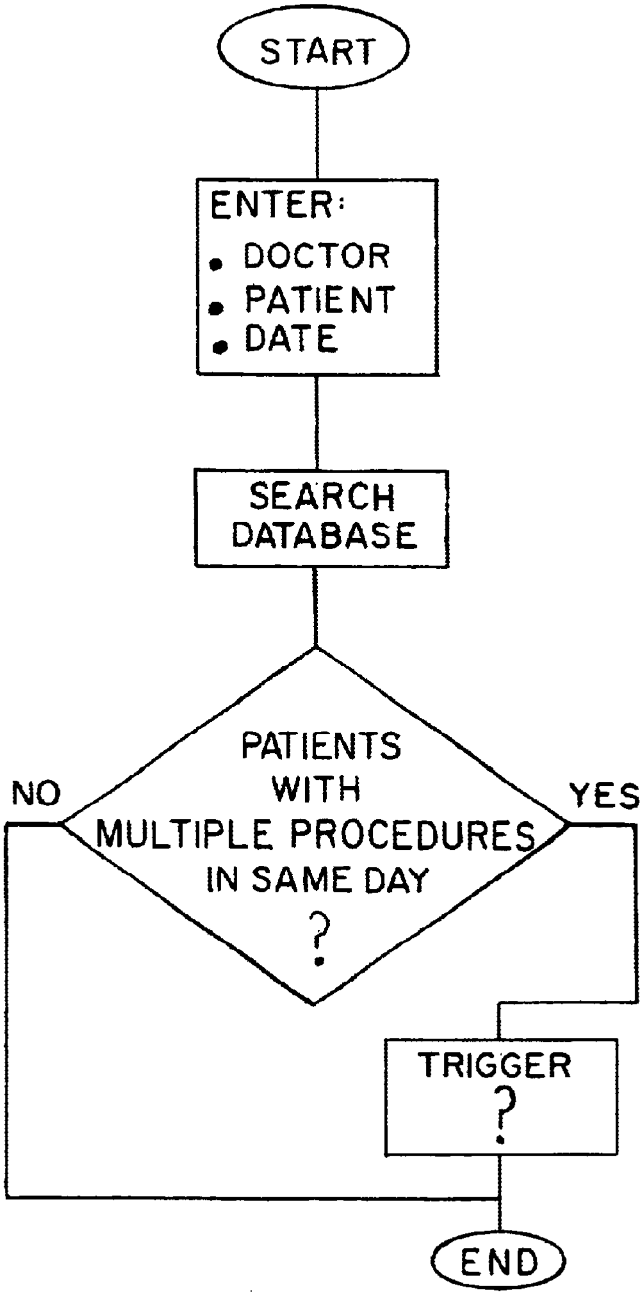
FIG. 7 is a Flow chart of a Trigger 3 identifying Improper Unbundling of single procedures into multiple procedures.

Another fraud-flag data processing trigger filter, identified as Trigger 3 in FIG. 7 herein, is an unbundling flag that compares the procedures reported by a health care provider, as performed on a single patient in a single episode of medical care, with an over-all treatment code covering the same health care rendition, to determine whether the health care provider has improperly reported and claimed payment for unbundled individual component parts of medical care rendered to a patient, rather than properly reporting and claiming payment for a single, and thus bundled, event of medical care rendition.

Figure 8:
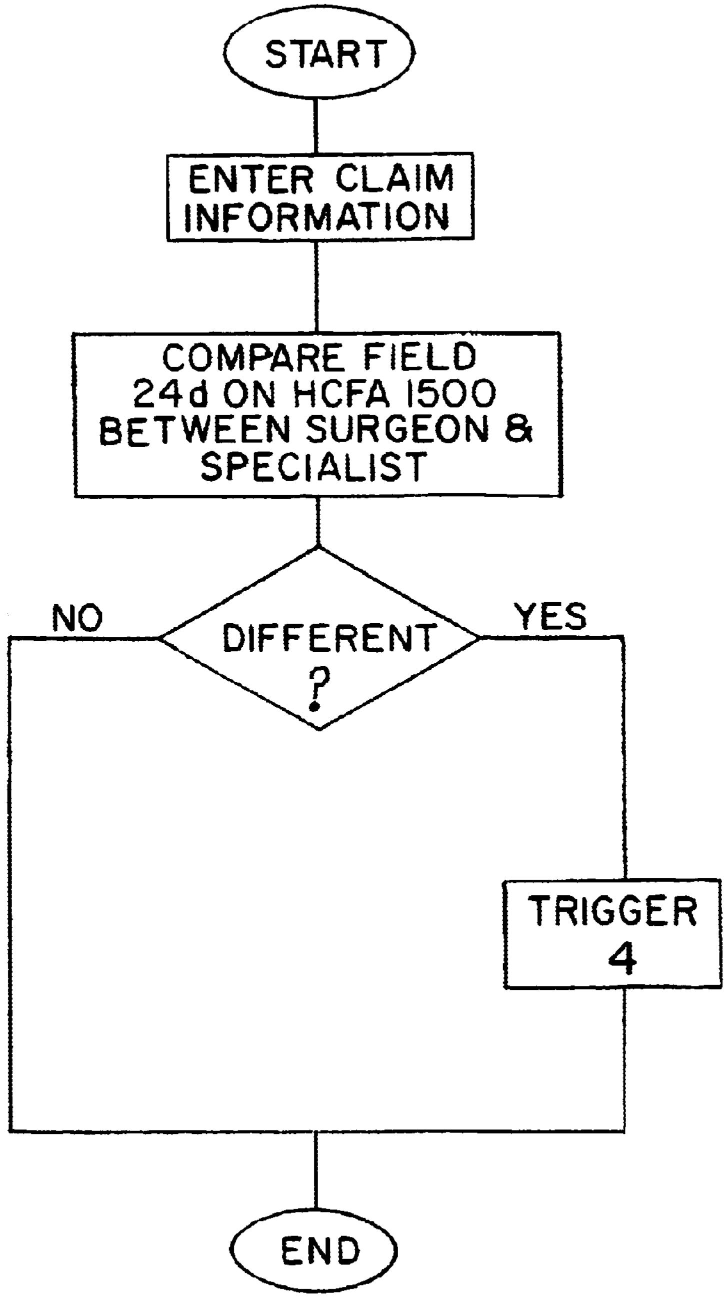
FIG. 8 is a Flow chart of a Trigger 4 identifying improper Upcoding of the identification code of a procedure to a different code for a different procedure.

Another fraud-flag data processing trigger filter, identified as Trigger 4 in FIG. 8 herein, is an upcoding flag that compares the procedures reported by a health care provider as having been performed on a single patient in a single episode of medical care with the reports of the same procedure independently furnished by other health care providers or surgical theater institutions to determine if the procedure reported by the individual claimant health care provider, whose claim is under review is properly the same as, or improperly different from, the procedure independently reported by other health care providers who rendered care in the same medical care rendition event to a similar patient at the same time and place.

Figure 9:
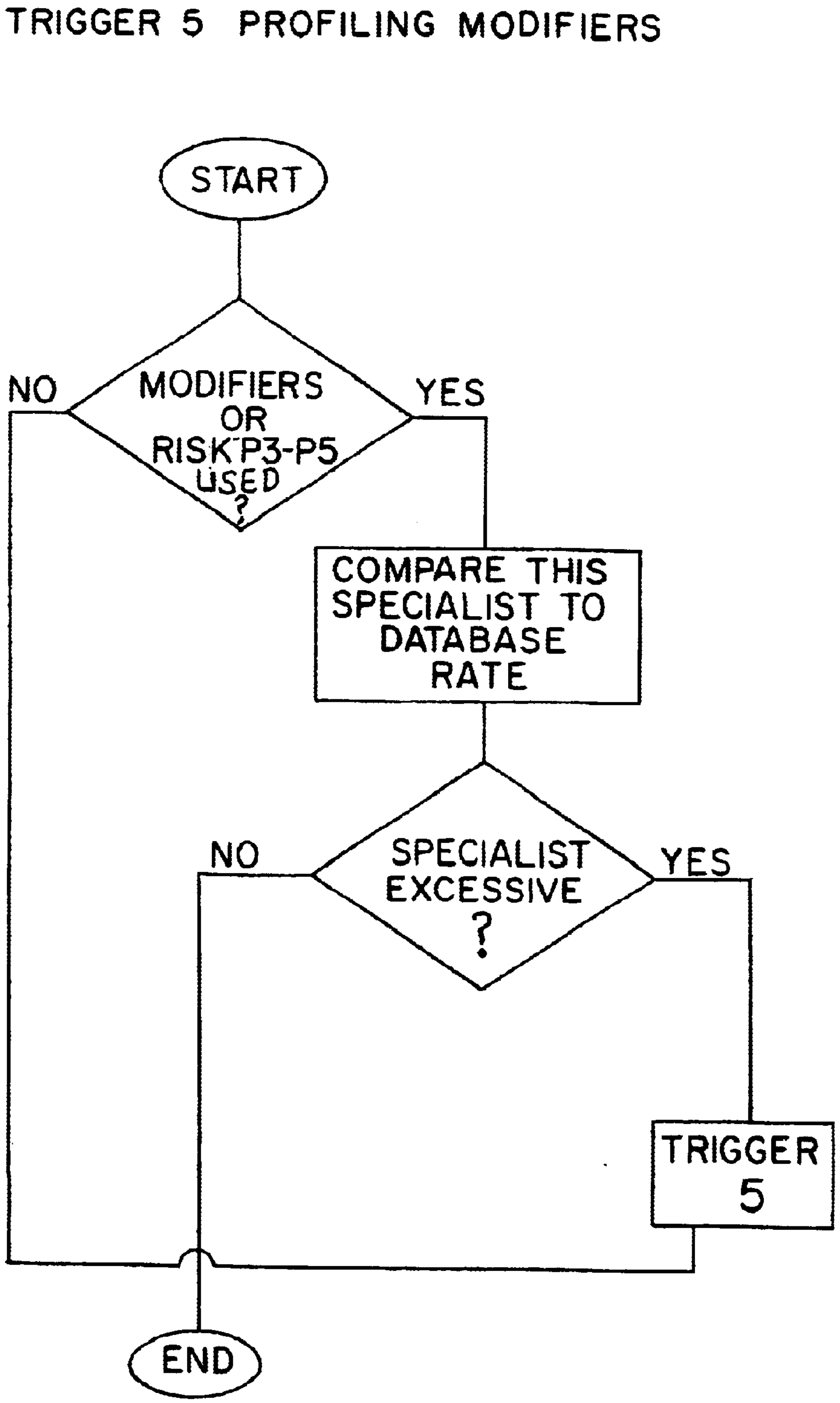
FIG. 9 is a Flow chart of a Trigger 5 identifying Profiling Modifiers.
Figure 10:
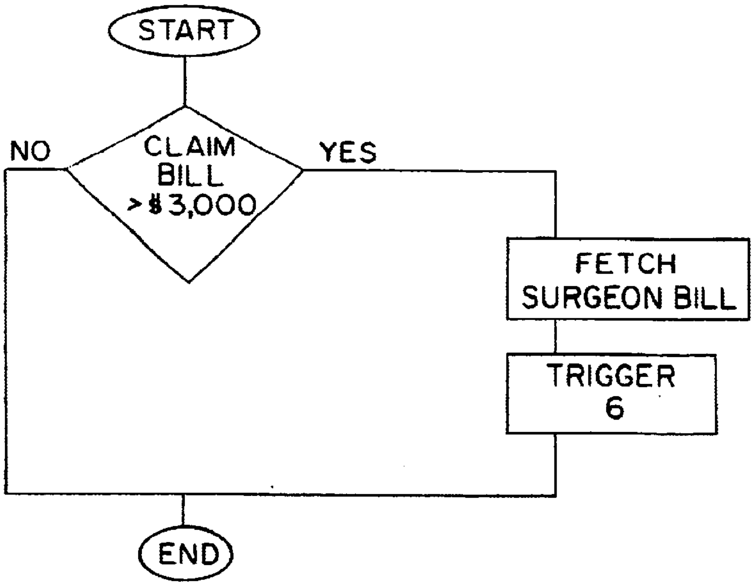
FIG. 10 is a Flow chart of a Trigger 6 identifying claims in excess of a $3000 Threshold.

Another fraud-flag trigger filter, identified as Trigger 5 as shown in FIG. 9, identifies profiling modifiers, which add to the value of a medical procedure, such as the increased risk of an ill patient, or the need for auxiliary procedures, such as extra monitoring, and determines if they are properly being claimed. By profiling the medical providers, it is able to determine if any are billing abusing, placing unnecessary monitoring or placing higher risk values to patients so they collect larger fees.

Furthermore, another fraud-flag data processing trigger filter, identified as Trigger 6, is a financial amount threshold flag that compares the monetary amount of a given health care provider claim for payment to a predetermined financial threshold, so as to flag those claims that are above the financial threshold, such as, for example, $3,000.

Figure 11:
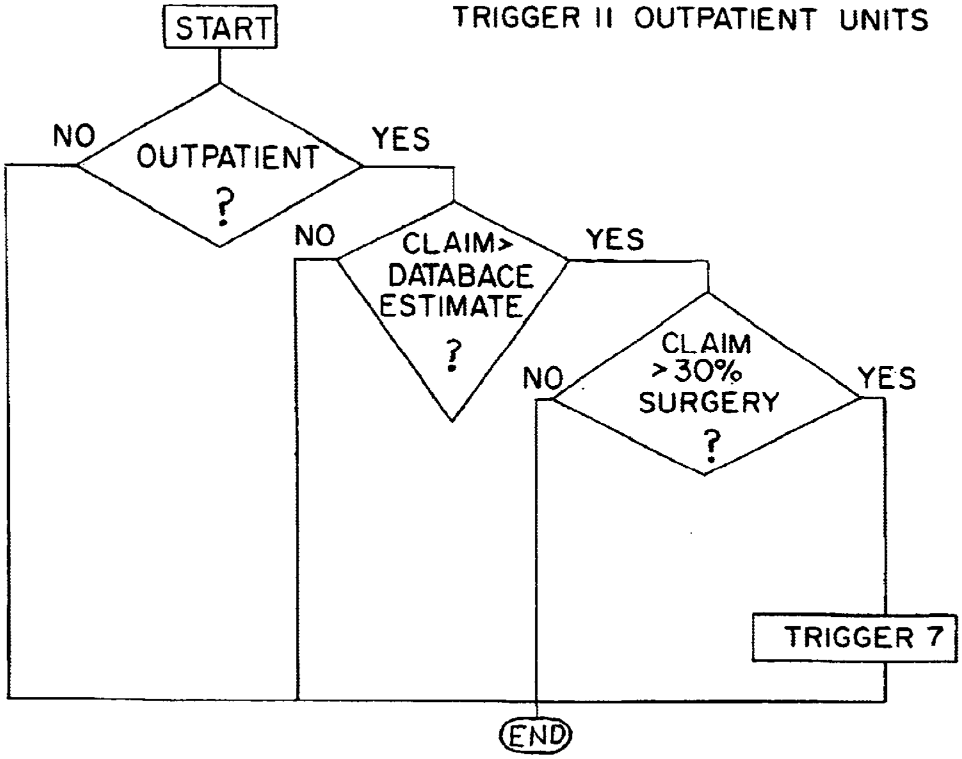
FIG. 11 is a Flow chart of a Trigger 7 identifying claims submitted on behalf of a provider at an Outpatient Unit.

Moreover, yet another fraud-flag data processing trigger filter, identified as trigger 7 in FIG. 11 herein, scrutinizes an outpatient non-JCAH facility data, to compare the site of health care rendition claimed by a provider in a payment claim, with a list of JCAH accredited health care facilities, so as to flag those sites in which health care being claimed for payment was performed outside a JCAH accredited facility where records are not kept as scrupulously as in a hospital.

Figure 12:
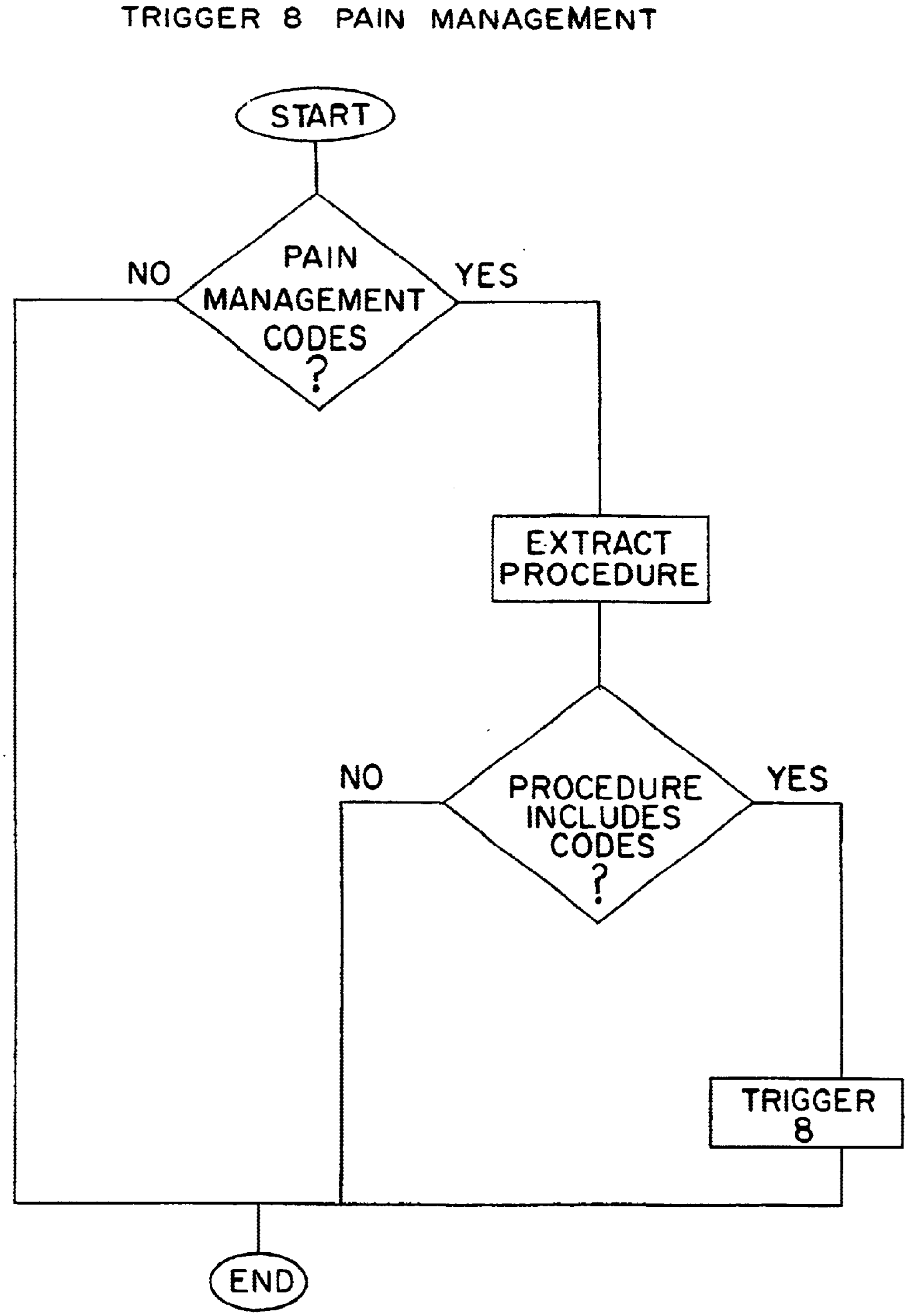

Another fraud-flag data processing trigger filter, identified as trigger 8 shown in FIG. 12 herein, is a pain management flag generated in response to data identified as representing the unbundling of pain management medical care events for which payment is claimed by individual health care providers.

Figure 13:
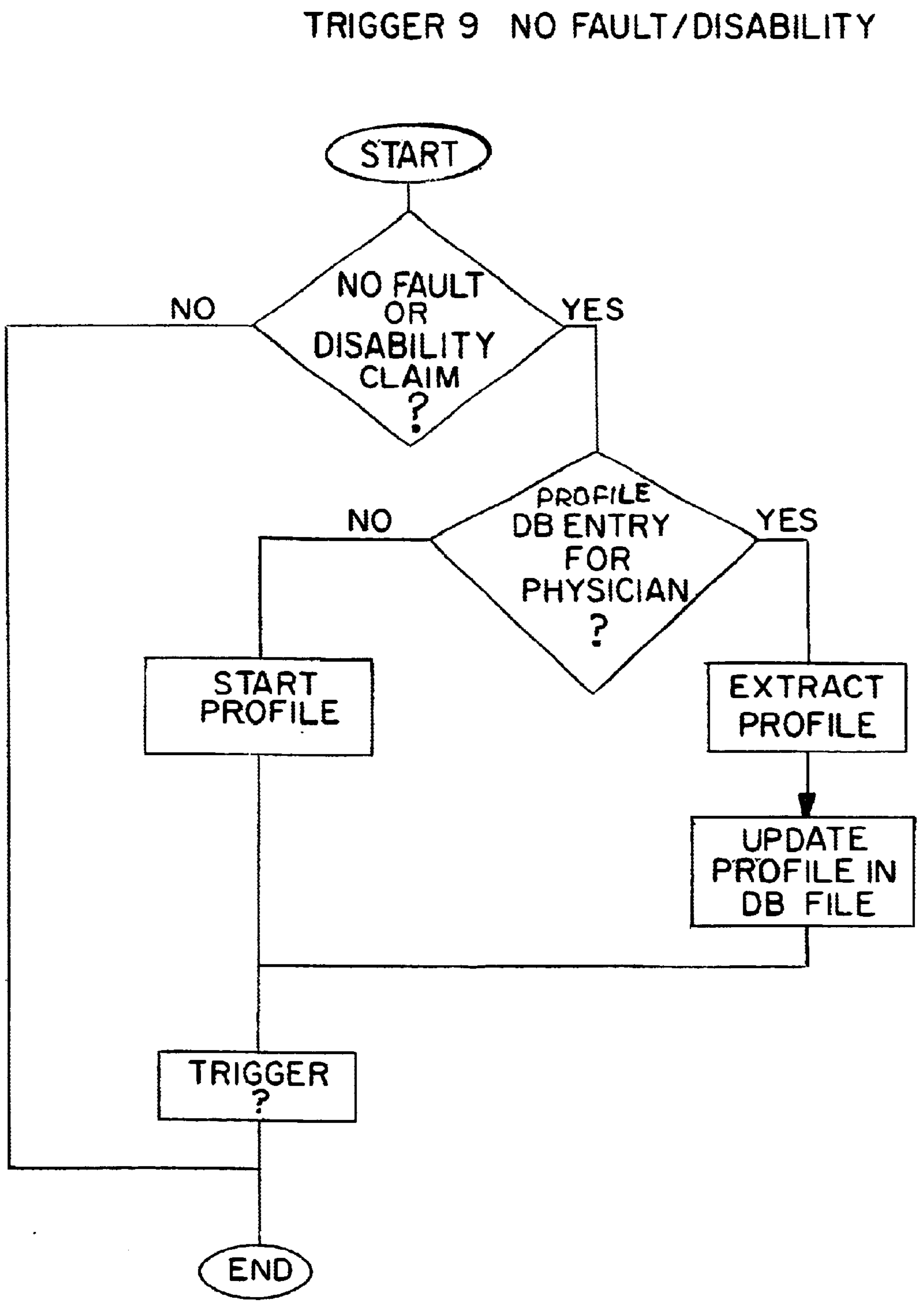
FIG. 13 is a Flow chart of a Trigger 9 identifying claims pertaining to No fault motor vehicle claims or personal disability claims.

A further fraud-flag data processing trigger filter, identified as Trigger 9 shown in FIG. 13 herein, analyzes no-fault Insurance Claims generated in response to data identified as representing the rendition of medical care events for a plurality of patients under claim for reimbursement.

For example, this trigger filter identifies a no-fault scheme of automobile insurance wherein the same diagnosis has been reported by and claimed for payment by a given health care provider for more than a predetermined number of patients in a pre-determined time period. This trigger filter also analyzes disability insurance claims wherein the same disability diagnosis has been reported by and claimed for payment by a given health care provider for more than a predetermined number of patients in a pre-determined time period.

The following is an example of the foregoing use of the flag trigger filters in the field of anesthesiology.

The time-difference flag compares the number of standard anesthesiology 15-minute time units, converted into absolute minutes by multiplying units ×15, with the absolute number of minutes reported by a surgical theater facility for the same procedure on the same patient within the same event-day (e.g., one calendar date or possibly two calendar dates if, for example, an emergency surgical procedure begins before midnight and ends after midnight).

This time-difference flag has a pre-determined selected number of standard deviations of absolute minutes of time difference report as between the anesthesiologist and the surgical theater facility wherein one standard deviation equals about 20 minutes; two standard deviations equals about 45 minutes; three standard deviations equals about 50 minutes; and four standard deviations equals about 60 minutes.

Furthermore, in anesthesiology claims the data processing trigger filter data identifies inconsistencies between an accumulated claim submission history of the individual anesthesiologist provider, with data compared to the normative health care parameters for the same anesthesiologist medical care events and procedures, derived from statistical normative data furnished by health care industry, insurance industry, and/or governmental health care insurance payer information databases.

The trigger filters may analyze normative health care parameters for anesthesiologist medical care events as to whether or not the anesthesiologist reported, in a plurality and pattern of claims for payment the following sub-procedures:

a) insertion of an arterial line;

b) use of a central venous pressure monitor;

c) utilization of controlled hypotension;

d) the coding or declaration of an emergency;

e) the use or recording of an American Society of Anesthesiologists (ASA) evaluation upgrade;

f) the use or coding by an anesthesiologist patient risk value in the range P3 through P5 inclusive where risk ratings include:

i) P1 representing a normal patient;

ii) P2 representing a patient with mild systemic disease;

iii) P3 representing a patient with severe systemic disease;

iv) P4 representing a patient in constant threat of death; and v) P5 representing a moribund patient not expected to survive 24 hours.

The financial amount threshold flag is calibrated to filter anesthesiologist claims for payment for dollar amounts that exceed about thirty percent of the dollar amount billed by a surgeon for the same procedure upon the same patient at the same place on the same event-day.

Another example is where health care provider fraud detection is directed to the field of medical pain management, wherein the unbundling modifier fraud-flag data processing trigger filter locates inconsistencies between accumulated claim submission history of a individual pain management health care provider and this data is compared to the normative health care parameters for the same pain management health care events and procedures derived from statistical normative data.

Such normative health care parameters for pain management health care events indicate whether or not the pain management provider reported, in a plurality and pattern of claims for payment, certain flagged procedures, such as:

a) x-rays of the spine;

b) fluoroscopy of the spine;

c) local anesthesia;

d) insertion of needle;

e) injection of steroid drugs; and f) sedation of the patient.

Additionally, the pain management provider is individually fraud-profiled by comparing aggregated multiple patient claim data from claims for payment for each above-enumerated pain management steps submitted by an individual pain management provider compared to the global, bundled treatment codes for such medical pain management procedures such as, for example, trigger point injections, lumbar nerve block, myelogram examinations, paravertebral nerve block and lumbar epidural procedures.

The data processing system of the present invention displays the aforementioned flagged fraud detection information, disclosed in the trigger filters, to a user visually and in printed form.

Software Of The Present Invention

With respect to the specific software to implement the system of the present invention, the present invention implements an application software whose purpose is to extract the suspicious medical claims from the databases of insurance companies. The project is comprised of multiple phases; the following example addresses the needs that are specific to phase I (anesthesiology). This application is referred to as the CAA (Claims Analysis Application).

Prerequisite Information Input

Sample Data

The system obtains a valid set of comparative test data.

Hospital Data (OSO/Per Se)

Hospital data is used as a comparison set to the claims data. It is used to create average measures that is compared to the claims data for analysis.

Insurance Data

Insurance company text files are used, such as by access to database schema beforehand and access to their DBMS system.

Staging Area

A relational staging area is used to store both the claims data that is provided by the abstraction layer and the reference data. An enhanced claims data model is built to store and partially process the triggers to produce the valuable information.

Proprietary Trigger Processing

At the heart of the system, comparative trigger procedure mines the claims data stored in the staging area. This data is mined based on the set of proprietary data processing filter triggers described above, which extract and flag for fraud the claims that are suspicious on a visual display means such as a computer monitor or in computer printed form. The first round of triggers are:

Trigger 1—Time Differences

The first trigger is based on extracting claims data from the claims database based on some criteria that is time based. The idea behind this is to find any discrepancies between the times recorded by the doctor and the hospital. This criteria is based on the following formula:

$$A = \text{Start Time (Anesthesiologist)} - \text{Start Time (Hospital)} = \#\ \text{minutes}$$

$$B = \text{End Time (Anesthesiologist)} - \text{End Time (Hospital)} = \#\ \text{minutes}$$

$$\text{Total Minutes} = A + B$$

Where:

Start Time is the begin time of the procedure

End Time is the end time of the procedure

Anesthesiologist is the time submitted by the Doctor to the insurance company

Hospital is the time submitted by the hospital to the insurance company

The Total Minutes is the time discrepancy between the doctor info and the claims info Deviation values are then calculated (based on the deviation table) as follows:

If the Total Minutes are:

>20 then deviation=1

>40 then Deviation=2

>60 then Deviation=3 and so on.

Trigger 2—Multiple Identifiers for Participators

The goal of this trigger is to scan the database and to pick doctors that are using various tax id # and addresses in order to make insurance claims. If a doctor is a Participator to a specific insurance plan, then the system identifies if this doctor is billing outside of his or her plan.

The system identifies a unique identifier for each doctor to apply this trigger in an effective manner. At his point, the Medicare numbers is a valid and unique identifier.

Trigger 3—Unbundling Multiple Procedures Per Day

The purpose of this trigger is to identify doctors that are performing more than one procedure per patient per day.

Trigger 4—(Upcoding) Pulling Out Certain Procedure Codes.

This trigger is a simple extraction of the claims that contain procedure codes.

Trigger 5—Extenders (Profiling Modifiers)

The aim of this trigger is extract claims that contain extra billable items. The system applies a count on this type of claims per doctor and compares the relative occurrence of these items to the systems reference database (when this information is available).

Trigger 6—Bills Over $3,000

This trigger extracts all the claims that are over $3,000.

Trigger 7—Outpatients

In this case, the goal is to extract claims that were made while the patients were not at the hospital. This trigger reviews the claims database table or another external data source to analyze where the patient was when a procedure occurred.

Other Triggers . . . 8 (Pain Management) and 9 (No Fault/Disability)

The system extracts the claims that are incomplete from the data integrity/referential integrity standpoint. In theory, this should already be taken care of by the insurance company operational system but the system of the present invention does not assume that these systems always follow the usual standards.

Essbase Analysis Server

The mined data is be stored into an Essbase application such as, for example, of Hyperion, Inc., that is used to perform reporting and analysis. Also, some of the trigger processing is performed with Essbase (when certain processing cannot be done in a Sequence Query Language (SQL) Server).

Proprietary Excel User Interface

A special interface reports and analyzes the suspicious claims information that has been processed by the system. This application interfaces with Essbase and the SQL Server.

Back-End Components

Production Manager

The role of these components is to manage the different sequential processes needed transform the initial data from the extract files and load it into the claims analysis Essbase database. A list of these processes include:

Load the extract files into the SQL Server staging area;

Apply the relevant triggers;

Load the data into the Essbase database;

Calculate the Essbase database; and,

Prepare the production reports.

Generic Excel Front-End Components

These components include all the low-level modules (Essbase retrieval automation, SQL Server connectivity, reporting routines, etc.) that are used to build custom front-ends for the different subject area.

General Relational Database Design

This creates the basic database schema for the SQL Server staging area. At this point, this schema is applicable to other subject areas.

Documentation

The documentation covers all the maintenance aspects of the back-end components.

The Triggers

Following is how the software treats the aforementioned triggers that need are implemented in the software.

Trigger 1—Time Differences

The first trigger is based on extracting claims data from the claims database based on some criteria that is time based. The idea behind this is to find any discrepancies between the times recorded by the doctor and the hospital. This criteria is based on the following formula:

$$A=\text{Start Time (Anesthesiologist)}-\text{Start Time (Hospital)}=\text{\# minutes}$$

$$B=\text{End Time (Anesthesiologist)}-\text{End Time (Hospital)}=\text{\# minutes}$$

$$\text{Total Minutes}=A+B$$

Where:

Start Time is the begin time of the procedure

End Time is the end time of the procedure

Anesthesiologist is the time submitted by the Doctor to the insurance company

Hospital is the time submitted by the hospital to the insurance company

The Total Minutes is the time discrepancy between the doctor info and the claims info Deviation values are then calculated (based on the deviation table) as follows:

If the Total Minutes are:

>20 then deviation=1

>40 then Deviation=2

>60 then Deviation=3 and so on. . .

Trigger 2—Multiple Identifiers for Participators

The goal of this trigger is to scan the database and to pick doctors that are using various tax id # and addresses in order to make insurance claims. If a doctor is a Participator to a specific insurance plan, the system identifies if this doctor is billing outside of his or her contractual plan.

A unique identifier for each doctor applies this trigger in an effective manner. For example, the Medicare number is a valid and unique identifier for the scrutinized providers.

Trigger 3—Multiple Procedures Per Day

The purpose of this trigger is to identify doctors that are performing more than one procedure per patient per day.

Trigger 4—Extenders

The aim of this trigger is extract claims that contain extra billable items. A count is applied on this type of claims per doctor and compare the relative occurrence of these items to the systems reference database.

Trigger 5—Bills Over $3,000

This trigger extracts all the claims that are over $3,000.

Trigger 6—Outpatients

In this case, the goal is to extract claims that were made while the patients were not at the hospital. The system reviews the claims database table or an external data source to analyze where the patient was when a procedure occurred.

Trigger 7—Pulling Out Certain Procedure Codes

This trigger is a simple extraction of the claims that contain procedure codes.

Other Triggers.

The system also extracts the claims that are incomplete from the data integrity/referential integrity standpoint. In theory, this should already be taken care of by the insurance company operational system but the system does not assume that these systems always follow the usual standards.

The Components and Implementation Tasks

The development of this system encompasses two types of activity; back-end development and subject area specific implementation. The back-end development includes all the elements that are used no matter what type of claims are analyzed. The subject area specific implementation relates to the elements that are specific to anesthesiology, such as the trigger implementation, the design of the Essbase database and part of the custom front-end development. The computer architecture facilitates the addition of new triggers and subject areas in the future. Following is a list of these tasks and their associated development time.

The Process

The software is used by a user who needs to transfer data from the insurance companies databases onto its own equipment from which the software performs the required analysis. The data is extracted from the sources system in a format that is compatible with the software.

To facilitate this task, the system elaborates the specifications of the different elements needed from the source databases. Ideally, the system asks the client to provide the data in the form of text file that could be easily loaded into the application. This approach has the advantage of transferring the data mapping and extraction tasks to the insurance company staff. It also minimizes the consulting work needed to do the initial implementation at a new client. If the client does not have the resources to perform the mapping and extraction, this work could be performed on a consulting basis by external resources.

High Level Architecture

The high level architecture shown in FIGS. 3 and 4 herein describe the proposed architecture for the claims Analysis.

Mapping & Extraction Layer

This portion of the solution requires that the insurance company provide a clear and concise extraction of their claims data based on requirements provided by the recovery analysis team. The provider is instructed on the specific columns that are required for the proper claims analysis.

From a preliminary study, the data that is provided by an insurance company contains the following elements:

Practitioner data (physicians info, coordinates,. . . ) Hospital data (location, specialty, . . . )

Diagnosis codes

Procedure codes

Time of procedure

Costs, Amounts, . . .

Abstraction Layer

The abstraction layer is a process that maps external claims data from insurance companies to the user's standard data model. This is used to separate the logical data model with the actual physical model that may have different naming conventions and/or different data types.

Hospital Information

Data is provided or acquired from the recovery analysis team's "reference data". This information is used to set average standards where physicians and procedures performed are scored on (known as standard deviations from the norm).

It is further noted that other modifications may be made to the present invention, without departing from the scope of the invention, as noted in the appended claims.

What is claimed is:

1. A data processing system for detecting health care provider fraud, comprising:

a. computer processor means for processing data;

b. computer storage means for storing data on a storage medium;

c. first means for initializing the storage medium;

d. second means for processing data regarding payment claims submitted by health care providers to payers wherein said payment claim data is processed to identify and flag fraud-suspect inconsistencies and anomalies regarding payments claims submitted for payment by health care providers;

e. third means for calibrating the processed data to enable appropriate identification of the fraud suspect inconsistencies and anomalies;

f. fourth means for fraud-profiling of individual health providers based on an accumulated history of claims submitted by an individual health care provider;

said data comprising an accumulated individual provider claim history of the individual health care provider;

said fourth means further comprises means for inputting, displaying, retrieving processing, comparing, filtering and storing on the storage medium i. data comprising an accumulated history of discrete data representing claims submitted for payment by an individual health care provider being profiled; and ii. subjecting said data comprising said accumulated individual provider claim history to at least one profiling modifier fraud-flag data processing filter, said profiling filter identifying and fraud-flagging inconsistencies between said accumulated claim submission history of said individual provider when those data are compared to the normative health care parameters for the same medical care events and procedures derived from statistical normative data furnished by health care industry, insurance industry, and/or governmental health care insurance payer information data bases.

2. A data processing system for detecting health care provider fraud, comprising:

a. computer processor means for processing data;

b. computer storage means for storing data on a storage medium;

c. first means for initializing the storage medium, d. second means for processing data regarding payment claims submitted by health care providers to payers wherein said payment claim data is processed to identify and flag fraud-suspect inconsistencies and anomalies regarding payments claims submitted for payment by health care providers;

e. third means for calibrating the processed data to enable appropriate identification of the fraud-suspect inconsistencies and anomalies; fourth means for fraud-profiling of individual health providers based on an accumulated history of claims submitted by an individual health care provider;

further wherein:

a. said first means further comprises means for inputting, displaying, retrieving processing, comparing, filtering and storing on the storage medium individual health care provider payment claim data; and b. said second means further comprises means for inputting, displaying, retrieving processing, comparing, filtering and storing on the storage medium data comprising at least one fraud-flag data processing filter to identify and flag fraud-suspect inconsistencies and anomalies regarding payment claims submitted for payment by health care providers; and c. said third means further comprises means for inputting, displaying, retrieving processing, comparing, filtering and storing on the storage medium calibrating data for said at least one fraud-flag data processing filter, said calibrating data comprising i. reference data regarding health care procedure billing parameters, said billing parameters data being furnished from health care industry, insurance industry, and/or governmental health care insurance payer information data bases; and d. said fourth means further comprises means for inputting, displaying, retrieving processing, comparing, filtering and storing on the storage medium i. data comprising an accumulated history of discrete data representing claims submitted for payment by an individual health care provider being profiled; and ii. subjecting said data comprising said accumulated individual provider claim history to at least one profiling modifier fraud-flag data processing filter, said profiling filter identifying and fraud-flagging inconsistencies between said accumulated claim submission history of said individual provider when those data are compared to the normative health care parameters for the same medical care events and procedures derived from statistical normative data furnished by health care industry, insurance industry, and/or governmental health care insurance payer information data bases.

3. A data processing system as in claim 2, wherein said second means further comprises:

a. at least one fraud-flag data processing filter further comprising a time-difference flag generated in response to a predetermined calibration threshold when the time duration reported on a payment claim by an individual health care provider for a patient care event is compared to an independently recorded measurement of the same time duration as reported by a hospital or other health care provider; and b. at least one fraud-flag data processing filter further comprising an unbundling flag comprised of comparing the procedures reported by a health care provider as performed on a single patient in a single episode of medical care with an over-all treatment code covering the same health care rendition to determine whether the health care provider has improperly reported and claimed payment for unbundled individual component parts of medical care rendered to a patient rather than properly reporting and claiming payment for a single, and thus bundled, event of medical care rendition;

c. at least one fraud-flag data processing filter further comprising a financial amount threshold flag wherein the monetary amount of a given health care provider claim for payment is compared to a predetermined financial threshold so as to flag those claims that are above the financial threshold;

d. at least one fraud-flag data processing filter further comprising an upcoding flag for comparing the procedures reported by a health care provider as having been performed on a single patient in a single episode of medical care with the reports of the same procedure independently furnished by other health care providers or surgical theater institutions to determine if the procedure reported by the individual claimant health care provider whose claim is under review is properly the same as or improperly different from the procedure independently reported by other health care providers who rendered care in the same medical care rendition event to the same patient at the same time and place;

e. at least one fraud-flag data processing filter further comprising an outpatient non-JCAH facility data processing filter to compare the site of health care rendition claimed by a provider in a payment claim with a list of JCAH accredited health care facilities, so as to flag those sites in which health care being claimed for payment was performed outside a JCAH accredited facility;

f. at least one fraud-flag data processing filter further comprising a multiple-provider-identity flag based on comparing the individual information identifying particular to health care providers with payment claims submitted by other health care providers having different addresses and different business entity names to determine if the same health care provider as identified by a never-varying Medicare provider number has submitted claims for payment for health care provided to patients under an improperly and superficial multiplicity of names and/or addresses purporting, within said superficial multiplicity to simultaneously be both a participant medical care provider and a non-participant provider under a particular contractual scheme of reimbursement, fraudulently appearing to the payer to entitlement to differing reimbursement rates by virtue of the improper multiplicity of claimed health care provider identities.

4. A data processing system as in claim 3, wherein said second means further comprises;

a. at least one fraud-flag data processing filter further comprising a pain management flag generated in response to data identified as representing the unbundling of pain management medical care events for which payment is claimed by individual health care providers; and b. at least one fraud-flag data processing filter further comprising a No-Fault Insurance Claim flag generated in response to data identified as representing the rendition of medical care events for a plurality of patients under claim for reimbursement under a no-fault scheme of automobile insurance wherein the same diagnosis has been reported by and claimed for payment by a given health care provider for more than a predetermined number of patients in a predetermined time period; and c. at least one fraud-flag data processing filter further comprising a Disability Insurance Claim flag generated in response to data identified as representing the rendition of medical care events for a plurality of patients under claim for reimbursement under a disability scheme of insurance wherein the same diagnosis has been reported by and claimed for payment by a given health care provider for more than a predetermined number of patients in a pre-determined time period.

5. A data processing system as in claim 4, wherein said health care provider fraud detection is directed to the field of medical pain management, and wherein:

a. said unbundling modifier fraud-flag data processing filter further comprises filtering data for and flagging inconsistencies between accumulated claim submission history of said individual pain management health care provider when those data are compared to the normative health care parameters for the same pain management health care events and procedures derived from statistical normative data furnished by health care industry, insurance industry, and/or governmental health care insurance payer information data bases; and wherein further said normative health care parameters for pain management health care events comprises a data filter for whether or not the pain management provider reported, in a plurality and pattern of claims for payment, at least one of:

i. X-Rays of the spine;
ii. fluoroscopy of the spine;
iii. local anesthesia;
iv. insertion of needle;
v. injection of steroid drugs; and
vi. sedation of the patient;

wherein further, said pain management provider will be individually fraud-profiled by comparing aggregated multiple patient claim data from claims for payment for each above-enumerated pain management steps submitted by an individual pain management provider compared to the global, bundled treatment codes for at least one of:

i. trigger point injections;
ii. lumbar nerve block;
iii. myelogram;
iv. paravertebral nerve block; and
v. lumbar epidural.

6. A data processing system as in claim 5, wherein resulting flagged fraud detection information is displayed to a user.

7. A data processing system as in claim 6, wherein resulting flagged fraud detection information is displayed visually and in printed form.

8. A data processing system as in claim 6, wherein said system is useable remotely by having means for inputting at a source computer of payment claim data; means for remote users to transmit said remote input claim data to a central processing computer located elsewhere by data communications means and means for returning the processed data, with flags fraud having been generated to said remote users said processed data being in visually displayable form, printable form, computer storable and computer readable form.

9. A data processing system as in claim 4, wherein resulting flagged fraud detection information is displayed to a user.

10. A data processing system as in claim 8, wherein resulting flagged fraud detection information is displayed visually and in printed form.

11. A data processing system as in claim 9, wherein said system is useable remotely by having means for inputting at a source computer of payment claim data; means for remote users to transmit said remote input claim data to a central processing computer located elsewhere by data communications means and means for returning the processed data, with flags fraud having been generated to said remote users said processed data being in visually displayable form, printable form, computer storable and computer readable form.

12. A data processing system as in claim 2, wherein said health care provider fraud detection is directed to the field of anesthesiology, and wherein:

a. said time-difference flag comprises a comparison of the number of standard anesthesiology 15-minute time units, converted into absolute minutes by multiplying units ×15, with the absolute number of minutes reported by a surgical theater facility for the same procedure on the same patient within the same event-day; and wherein i. said calibration of said time-difference flag comprises a pre-determined selected number of standard deviations of absolute minutes of time difference report as between the anesthesiologist and the surgical theater facility wherein 1 standard deviation comprises about 20 minutes; two standard deviations comprises about 45 minutes; three standard deviations comprises about 50 minutes; and four standard deviations comprises about 60 minutes;

b. said profiling modifier fraud-flag data processing filter further comprises filtering data for and flagging inconsistencies between accumulated claim submission history of said individual anesthesiologist provider when those data are compared to the normative health care parameters for the same anesthesiologist medical care events and procedures derived from statistical normative data furnished by health care industry, insurance industry, and/or governmental health care insurance payer information data bases; and wherein further said normative health care parameters for anesthesiologist medical care events comprises a data filter for whether or not the anesthesiologist reported, in a plurality and pattern of claims for payment, at least one of:

i. insertion of an arterial line;
ii. use of a central venous pressure monitor;
iii. utilization of controlled hypertension;
iv. the coding or declaration of an emergency;
v. the use or recording of an American Society of Anesthesiologists (ASA) evaluation upgrade; and,
vi. the use or coding by an anesthesiologist patient risk value in the range P3 through P5 inclusive where risk ratings comprise P1 representing a normal patient; P2 representing a patient with mild systemic disease; P3 representing a patient with severe systemic disease; P4 representing a patient in constant threat of death; and P5 representing a moribund patient not expected to survive 24 hours; and, c. a financial amount threshold flag is calibrated to filter anesthesiologist claims for payment for dollar amounts that exceed a predetermined amount of the dollar amount billed by a surgeon for the same procedure upon the same patient at the same place on the same event-day.

* * * * *